United States Patent
Goto et al.

(10) Patent No.: US 8,633,199 B2
(45) Date of Patent: Jan. 21, 2014

(54) MEDICINE CONSISTING OF CONCOMITANT USE OR COMBINATION OF DPP-IV INHIBITOR AND OTHER DIABETIC MEDICINE

(75) Inventors: Moritaka Goto, Nagoya (JP); Satoko Yamashita, Nagoya (JP); Keizo Nakaya, Nagoya (JP); Tetsushi Tomoguri, Nagoya (JP); Tsutomu Ishida, Nagoya (JP); Masahiro Fuchigami, Nagoya (JP)

(73) Assignee: Sanwa Kagaku Kenkyusho Co., Ltd., Nagoya-Shi (JP)

( * ) Notice: Subject to any disclaimer, the term of this patent is extended or adjusted under 35 U.S.C. 154(b) by 318 days.

(21) Appl. No.: 12/988,541

(22) PCT Filed: May 12, 2009

(86) PCT No.: PCT/JP2009/058803
§ 371 (c)(1),
(2), (4) Date: Dec. 2, 2010

(87) PCT Pub. No.: WO2009/139362
PCT Pub. Date: Nov. 19, 2009

(65) Prior Publication Data
US 2011/0071166 A1    Mar. 24, 2011

(30) Foreign Application Priority Data
May 14, 2008  (JP) ................................ 2008-127480

(51) Int. Cl.
*A61K 31/519*  (2006.01)
*A61P 3/10*  (2006.01)
*A61P 3/00*  (2006.01)

(52) U.S. Cl.
USPC ..................................................... 514/259.3

(58) Field of Classification Search
USPC ..................................................... 514/259.3
See application file for complete search history.

(56) References Cited

U.S. PATENT DOCUMENTS

| | | | |
|---|---|---|---|
| 7,345,180 B2 * | 3/2008 | Kakigami et al. | ............ 548/453 |
| 2003/0139434 A1 | 7/2003 | Balkan et al. | |
| 2003/0166578 A1 | 9/2003 | Arch et al. | |
| 2006/0205675 A1 | 9/2006 | Arch et al. | |
| 2006/0210627 A1 * | 9/2006 | Pfeffer et al. | ................. 424/464 |
| 2006/0229286 A1 | 10/2006 | Kakigami et al. | |
| 2007/0238756 A1 | 10/2007 | Arch et al. | |
| 2008/0076811 A1 | 3/2008 | Balkan et al. | |
| 2009/0042863 A1 | 2/2009 | Takeuchi et al. | |
| 2009/0082256 A1 | 3/2009 | Abe et al. | |

FOREIGN PATENT DOCUMENTS

| | | |
|---|---|---|
| WO | 01/52825 A1 | 7/2001 |
| WO | 01/97808 A1 | 12/2001 |
| WO | 2004/067509 A1 | 8/2004 |
| WO | 2006/129785 A1 | 12/2006 |
| WO | 2007/074884 A1 | 7/2007 |

OTHER PUBLICATIONS

Kazuto Yamazaki et al., "*Comparison of Efficacies of a Dipenptidyl Peptidase IV Inhibitor and α-Glucosidase Inhibitors in Oral Carbohydrate and Meal Tolerance Tests and the Effects of Their Combination in Mice*," Journal of Pharmacological Sciences, 104, May 8, 2007, pp. 29-38.

Bo Ahren et al., "*Twelve- and 52-Week Efficacy of the Dipeptidyl Peptidase IV Inhibitor LAF237 in Metformin-Treated Patients with Type 2 Diabetes*," Diabetes Care, vol. 27, No. 12, Dec. 2004, pp. 2874-2880.

* cited by examiner

*Primary Examiner* — Yong Chong
*Assistant Examiner* — Jason A Deck
(74) *Attorney, Agent, or Firm* — Burr & Brown, PLLC (57) ABSTRACT

The problem to be solved by the present invention is to provide a medicine which is excellent in the treatment of type 2 diabetes, diabetic complications or impaired glucose tolerance. The present invention provides a medicine characterized in that a compound represented by the following general formula (I), a salt thereof, or a solvate thereof, and at least one kind of other diabetic medicine:

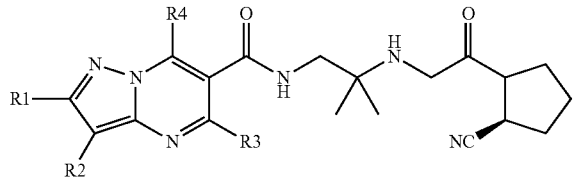

(wherein $R^1$, $R^2$, $R^3$ and $R^4$ are each a hydrogen atom, a trifluoromethyl group or a C1-3 alkyl group).

10 Claims, 4 Drawing Sheets

MEDICINE CONSISTING OF CONCOMITANT USE OR COMBINATION OF DPP-IV INHIBITOR AND OTHER DIABETIC MEDICINE

TECHNICAL FIELD

The present invention relates to a medicine consisting of concomitant use or combination of (S)—N-(2-(2-(2-cyanopyrrolidin-1-yl)-2-oxoethylamino)-2-methylpropyl)-2-methylpyrazolo[1,5-a]pyrimidine-6-carboxamide, which is a DPP-IV inhibitor, or an analogue thereof, and other diabetic medicine.

BACKGROUND OF THE INVENTION

Diabetes is a condition in which a glucose concentration in blood (blood glucose level) has increased abnormally, and suitable control of a blood glucose level is required. A typical therapeutic agent for diabetes is a sulfonylurea agent (hereinafter described as an SU agent), which is also used concomitantly with other therapeutic agent for diabetes. However, it is known that the SU agent causes hypoglycemia as a side effect. Furthermore, it is also concerned that use of the SU agent for a long period leads to fatigue of pancreatic β cells.

An example of hormones which are involved in the change of a glucose concentration in blood may include glucagon-like peptide-1 (hereinafter described as GLP-1) and gastric inhibitory peptide (hereinafter described as GIP). GLP-1 and GIP are a peptide which is secreted from a gastrointestinal tract with a diet, acts on pancreatic βcells to accelerate blood glucose-dependent insulin secretion, and maintains homeostasis of glucose metabolism via acceleration of the generation and secretion of insulin based on the protection or improvement of the function of βcells, suppression of the secretion of glucagon, retardation of gastric emptying, and the like, whereby leads to enhancement of an effect of insulin in the periphery. However, since GLP-1 and GIP are rapidly decomposed by dipeptidyl peptidase IV (hereinafter described as DPP-IV) in circulating blood and inactivated, it may not exhibit its effect sufficiently in vivo.

DPP-IV inhibitors suppress the metabolism of endogenous GLP-1 and GIP, and retain the effect of these. Therefore, they show promise for blood glucose concentration-dependent therapeutic agents for type 2 diabetes, and an effect of protecting pancreatic βcells, which seems to be caused by increase in the concentration of active GLP-1 and GIP, is expected in a long-term administration.

However, since it is considered that acceleration of insulin secretion by GIP is diminished in a patient with type 2 diabetes, the contribution of GIP to the effect of the DPP-IV inhibitor to accelerate insulin secretion in the patient is unclear. On the other hand, it is suggested by studies using receptor gene-deficient animals and the like that GIP may induce obesity or evoke insulin resistance.

For DPP-IV inhibitors, a treatment method for trying to control blood glucose by concomitant use with other diabetic medicine is known (Patent Document 1). For example, there has been reported that approaches to control blood glucose by concomitant use of E3024 trifluoro acetate, which is a DPP-IV inhibitor, with Voglibose (Non-patent Document 1), concomitant use of LAF237 with Metformin (Non-patent Document 2), concomitant use of 2-[[6-[(3R)-3-amino-1-piperidinyl]-3,4-dihydro-3-methyl-2,4-dioxo-1(2H)-pyrimidinyl]methyl]-4-fluorobenzonitrile or 2-[2-(3-(R)-aminopiperidin-1-yl)-5-fluoro-6-oxo-6H-pyrimidin-1-ylmethyl]benzonitrile with Voglibose (Patent Document 2), and concomitant use of 3-{2S,4S}-4-[4-(3-methyl-1-phenyl-1H-pyrazol-5-yl)piperadin-1-yl]pyrrolidin-2-ylcarbonyl}thiazolidine with Voglibose (Patent Document 3).

However, they all relate to concomitant use of a specific compound having a DPP-IV inhibitory effect and other diabetic medicine, and a specific description and an effect of treating diabetes with respect to concomitant use of (S)—N-(2-(2-(2-cyanopyrrolidin-1-yl)-2-oxoethylamino)-2-methylpropyl)-2-methylpyrazolo[1,5-a]pyrimidine-6-carboxamide or an analogue thereof as a DPP-IV inhibitor and other diabetic medicine are not known.

Patent Document 1: WO01/052825
Patent Document 2: WO2007/074884
Patent Document 3: WO2006/129785
Non-patent Document 1: Yamazaki, K. et al., Journal of Pharmacological Sciences, 104, 29-38 (2007).
Non-patent Document 2: Ahren, B. et al., Diabetes Care, 27, 2874-80 (2004).

SUMMARY OF THE INVENTION

Problem to be Solved by the Invention

The problem to be solved by the present invention is to provide a medicine which is excellent in the treatment of type 2 diabetes, diabetic complications or impaired glucose tolerance.

Means for Solving the Problem

The inventors of the present invention have done studies based on the above, and consequently found that an effect of suppressing increase in blood glucose is shown without secretion of excess insulin during concomitant use or combination of (S)—N-(2-(2-(2-cyanopyrrolidin-1-yl)-2-oxoethylamino)-2-methylpropyl)-2-methylpyrazolo[1,5-a]pyrimidine-6-carboxamide (hereinafter referred to as compound (I)) or an analogue thereof with an α-glucosidase inhibitor such as Miglitol, or during concomitant use or combination with a biguanide drug such as Metformin, and completed the present invention. And then, a high concentration of an active GLP-1 is maintained and an increase in the concentration of GIP is suppressed.

Namely, the present invention is as follows.

(1) A medicine characterized in that a compound represented by the following general formula (I), a salt thereof, or a solvate thereof, and at least one kind of other diabetic medicine are concomitantly administered:

(wherein $R^1$, $R^2$, $R^3$ and $R^4$ are each a hydrogen atom, a trifluoromethyl group or a C1-3 alkyl group).

(2) A medicine comprising a combination of a compound represented by the general formula (I), a salt thereof, or a solvate thereof, and at least one kind of other diabetic medicine.

(wherein $R^1$, $R^2$, $R^2$ and $R^4$ are each a hydrogen atom, a trifluoromethyl group or a C1-3 alkyl group).

(3) The medicine according to (1) or (2), which is for the treatment of type 2 diabetes, diabetic complications, impaired glucose tolerance, insulin resistance, or obesity.

(4) The medicine according to (1) or (2), wherein the compound represented by the general formula (I) is (S)—N-(2-(2-(2-cyanopyrrolidin-1-yl)-2-oxoethylamino)-2-methylpropyl)-2-methylpyrazolo[1,5-a]pyrimidine-6-carboxamide.

(5) The medicine according to (1) or (2), wherein the other diabetic medicine is selected from an agent for improving hepatic glucose metabolism and an agent for inhibiting absorption of sugar.

(6) The medicine according to (5), wherein the agent for improving hepatic glucose metabolism is a biguanide.

(7) The medicine according to (6), wherein the biguanide is Metformin or a salt thereof.

(8) The medicine according to (5), wherein the agent for inhibiting absorption of sugar is an α-glucosidase inhibitor.

(9) The medicine according to (8), wherein the α-glucosidase inhibitor is Miglitol.

Effect of the Invention

According to the medicine of the present invention, increase of blood glucose can be suppressed without secretion of excess insulin, whereby blood glucose is suitably controlled, as compared to the case where the DPP-IV inhibitor or other diabetic medicine used in the present invention is singly administered. Thus, pancreatic exhaustion is alleviated and an excellent action of protecting pancreas is exhibited. Furthermore, the concentration of GLP-1 is increased synergistically, whereby the concentration of the active GLP-1 in blood can be highly maintained. Thus, an action of accelerating neogenesis or replication of pancreatic βcells, or an action of lowering body weight can be expected. Furthermore, increase of the blood concentration of GIP can be suppressed. Since GIP may induce obesity or worsen insulin resistance, an action of lowering body weight and an action of improving insulin resistance can be expected by suppressing increase of the concentration of GIP in blood.

Therefore, the present invention can provide a medicine which is excellent as a therapeutic agent for type 2 diabetes, diabetic complications, impaired glucose tolerance, insulin resistance or obesity.

DESCRIPTION OF THE INVENTION

The compound of the general formula (I), the compound (I) or an analogue thereof are compounds of the present invention having a DPP-IV inhibitory activity described in WO2004/067509, and can be prepared according to the synthesis methods described in that document. The salts of these compounds can also be formed with referring to the abovementioned WO2004/067509 and the technical common knowledge. A solvate is a compound to which a solvent is bound, and when the solvent is water, it is sometimes specifically described as a hydrate.

The other diabetic medicine includes active ingredients which are used as diabetic medicine except DPP-IV inhibitors, pharmaceutically acceptable salts thereof and solvates thereof. When such diabetic medicine are specified in view of a mechanism of action, examples thereof may include an agent for improving hepatic glucose metabolism, an agent for inhibiting absorption of sugar, and the like.

Examples of the agent for improving hepatic glucose metabolism may include biguanides (e.g.; Metformin, Buformin, Phenformin), glucose-6-phosphatase inhibitors, fructose-1,6-bisphosphatase inhibitors (e.g.; CS-917) glycogen phospholylase inhibitors (e.g.; CP-91149), glucagon receptor antagonists (e.g.; BAY27-9955), phosphoenolpyruvate carboxykinase inhibitors, pyruvate dehydrogenase kinase inhibitors, and the like.

Examples of the agent for inhibiting absorption of sugar may include inhibitors of gastric emptying (e.g.; amylin, pramlintide which is an amylin analogue), α-glucosidase inhibitors (e.g.; Voglibose, Acarbose, Miglitol), inhibitors of sodium-glucose co-transporters (SGLT) (e.g.; Dapagliflozin, T-1095), and the like.

Among these diabetic medicine, biguanides or α-glucosidase inhibitors are preferable. Furthermore, Metformin is preferable as biguanides, and Miglitol is preferable as α-glucosidase inhibitors.

In the medicine of the present application invention, the active ingredients thereof may be incorporated in separate formulations as a plurality of formulations, or may be incorporated in the same formulation as one formulation.

The "medicine characterized by administering concomitantly" refers to a medicine which is expected to be administered in the concomitant use. The "administering concomitantly" refers to a medicine in which a plurality of medicines or the active ingredients thereof are administered to a patient, preferably, substantially simultaneously. The medicine comprising a combination refers to a medicine which is expected to be administered in combination, i.e., a medicine which is expected to be administered in the above-mentioned concomitant use. In the medicine of the present invention, the case when the active ingredients to be administered are included in separate formulations as a plurality of formulations is not necessarily limited to the case when the plurality of formulations are administered at the same time. The administration method is not specifically limited so long as the periods at which respective drugs maintain their blood effective concentrations are overlapped. Generally, each formulation is administered according to its original method for administration. Therefore, the numbers of times of administration thereof may be the same or different.

Examples of the manner of administration of the medicine of the present invention may include 1) administration of a single formulation which is obtained by simultaneously formulating the active ingredient of the other diabetic medicine, and the compound of the general formula (I) or an analogue thereof, 2) simultaneous administration of two kinds of formulations obtained by separately formulating the active ingredient of the other diabetic medicine, and the compound of the general formula (I) or an analogue thereof, in the same administration route, 3) staggered administration of two kinds of formulations obtained by separately formulating the active ingredient of the other diabetic medicine, and the compound of the general formula (I) or an analogue thereof in the same administration route, 4) simultaneous administration of two kinds of formulations obtained by separately formulating the active ingredient of the other diabetic medicine, and the compound of the general formula (I) or an analogue thereof in the different administration routes, 5) staggered administration of two kinds of formulations obtained by separately formulating the active ingredient of the other diabetic medicine, and the compound of the general formula (I) or an analogue thereof in the different administration routes (for example, administration in the order of the active ingredient for the other diabetic medicine and the compound of the general formula (I) or an analogue thereof, or administration in the reverse order), and the like.

The medicinal effect exhibited by administering the medicine of the present invention can be evidenced by, for example, by using a known corresponding pharmacological model. Namely, a person skilled in the art can confirm beneficial effects on the above-mentioned and below-mentioned indications to be treated by selecting a related animal test model. Namely, the experiments as mentioned below show that the medicine of the present invention can specifically provide a treatment effect in an enhanced or synergistic manner.

The medicine of the present invention is effective as a therapeutic and/or prophylactic agent for type 2 diabetes, diabetic complications, impaired glucose tolerance, insulin resistance or obesity or the like. In these patients, effectiveness on hyperglycemia, impaired fasting plasma glucose and the like by correction of glycemic control can specifically be expected. Furthermore, effectiveness on metabolic syndrome and the like by a body weight lowering action, or effectiveness on hyperinsulinemia, hypertriglyceridemia, or insulin resistance glucose metabolism disorder or the like by an insulin resistance improving action can be expected.

A further advantage of the medicine of the present invention may be that the dose of the drug may be decreased by using individual drugs to be combined in low doses. With respect to this, examples of the advantages may include not only that only a small amount of dose is required, but also frequency of applications can be decreased, or generation of side effects can be decreased, and the like.

For the formulation of the medicine of the present invention, as mentioned above, the plurality of active ingredients may be included as the plurality of formulations in separate formulations, or may be included in the same formulation as one formulation, and in both cases, formulation can be carried out by using the excipients and the like mentioned below. The dosage form of the medicine of the present invention, oral agents which are excellent in convenience or compliance are preferable, it is not limited to these.

The dose of the medicine of the present invention may be similar to a general dose of the active ingredient of the other diabetic medicine or the compound (I), and may be suitably selected according to the object of administration, administration route, objective disease, dosage form and the like. The ratio of the dose of the active ingredient of the other diabetic medicine to the compound (I) is naturally determined according to the respective doses.

Generally, when the medicine of the present invention is administered orally, the dose of the compound of the general formula (I) is, for example, generally 0.1 to 2000 mg/day, preferably 1 to 1000 mg/day, more preferably 50 to 800 mg/day per an adult human patient (body weight: 60 kg). The dosage of the compound (I) is also similar. This amount may also be administered in two or three portions a day.

The dose of the active ingredient in the other diabetic medicine varies according to the drug. When the biguanides is used, the dose thereof is generally 25 to 5000 mg/day, preferably 50 to 3000 mg/day per an adult patient (body weight: 60 kg), and when the α-glucosidase inhibitor is used, the dose thereof is generally 0.01 to 1000 mg/day, preferably 0.1 to 500 mg/day per an adult patient (bodyweight: 60 kg). Specifically, when the biguanides is Metformin, the effective amount of Metformin is generally 125 to 5000 mg/day, preferably 250 to 3000 mg/day per an adult human patient (body weight: 60 kg). Furthermore, when the α-glucosidase inhibitor is Miglitol, the effective amount of Miglitol is generally 25 to 500 mg/day, preferably 50 to 250 mg/day per an adult patient (body weight: 60 kg), and when the α-glucosidase inhibitor is Voglibose, the dose thereof is generally 0.1 to 2 mg/day, preferably 0.2 to 1 mg/day per an adult patient (body weight: 60 kg).

EXAMPLES

The present invention is explained in more detail by the following Experimental Examples, but they do not limit the present invention and may be modified to the extent that they do not depart from the scope of the present invention.

Experimental Example 1

Effects of compound (I) alone, Miglitol alone and concomitant use of compound (I) and Miglitol on plasma concentration of active GLP-1 during oral sucrose loading test in Slc: Zucker-fa/fa rats (hereinafter abbreviated as Zucker fatty rats)
(Test Method)

An operation to insert a polyurethane catheter was performed on the right jugular vein of a Zucker fatty rat (9 weeks old, male, Japan SLC, Inc.) which is an obesity-insulin resistant model, and experiments were performed in the following four groups.

(1) Control group: purified water was administered at a ratio of 5 ml/kg (2) Compound (I) group: the compound (I) dissolved in purified water was administered at a dose of 3 mg/kg (5 ml/kg)

(3) Miglitol group: Miglitol dissolved in purified water was administered at a dose of 3 mg/kg (5 ml/kg)

(4) Concomitant use group: the compound (I) and Miglitol dissolved in purified water were administered at respective dose of 3 mg/kg (5 ml/kg)

Figure 1:
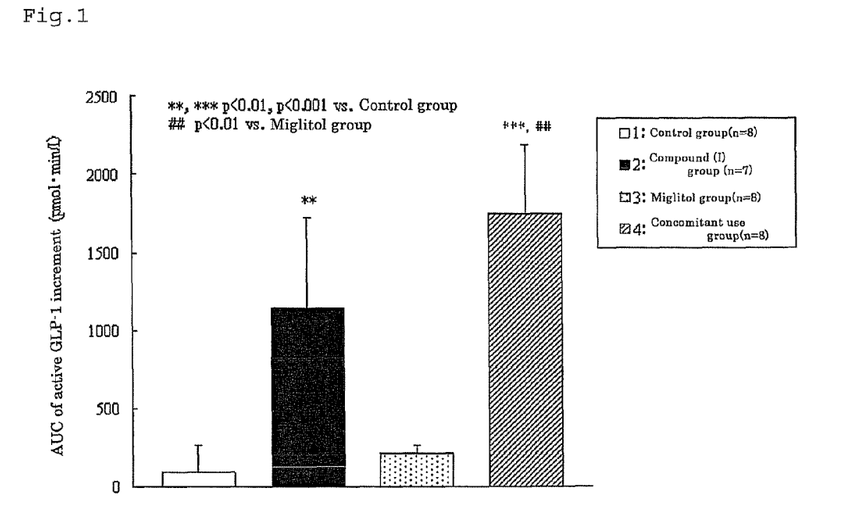
FIG. 1 is a graph showing the actions of the compound (I) alone, Miglitol alone and concomitant use of the compound (I) and Miglitol on the change in the increase of the plasma concentration of active GLP-1 after oral sucrose loading in Zucker fatty rats.

Purified water, the compound (I) and Miglitol were orally administered respectively to the Zucker fatty rats fasted overnight in each group as described in (1) to (4), and after 15 minutes, a 30% aqueous sucrose solution was administered at a ratio of 10 ml/kg. Blood was collected from the catheter immediately before administration and after administration of sucrose, and centrifuged at 4° C., 3000 rpm for 10 minutes to obtain plasma. The concentration of an active GLP-1 in the obtained plasma was measured by an enzyme immunoassay (hereinafter abbreviated as ELISA) (GLUCAGON-LIKE PEPTIDE-1 (ACTIVE) ELISA KIT, LINCO Research, Inc., US). Based on the measured concentration of the active GLP-1 in the plasma, the amount of change relative to the concentration immediately before administration of sucrose was obtained, and an area under curve (hereinafter abbreviated as AUC) from immediately before the administration of sucrose to 120 minutes after the administration was calculated. The result of calculation is shown in FIG. 1. Each column in figure shows an average value (n=8 in Groups 1, 3 and 4, n=7 in Group 2)±a standard deviation.

(Results)
Concentration of Active GLP-1

In the oral sucrose loading tests to Zucker fatty rats, there was no significant difference in the increase of the concentration of the active GLP-1 in the plasma by administration of Miglitol, whereas the compound (I) increased the concentration significantly. Furthermore, when the compound (I) and Miglitol were used concomitantly, the concentration of the active GLP-1 in the plasma was increased more than that when the compound (I) was used alone, and the degree thereof was synergistic. Namely, it is shown that an action of accelerating neogenesis or replication of pancreatic β cells or an action of lowering body weight can be expected by the concomitant use of the compound (I) and Miglitol.

Experimental Example 2

Effects of compound (I) alone, Miglitol alone and concomitant use of compound (I) and Miglitol on GIP, glucose and insulin concentrations in plasma during liquid diet loading test in Crlj: ZUC-Lepr$^{fa}$ Genotype: fa/fa rats (hereinafter abbreviated as Zucker fatty rats)

(Test Method)

An operation to insert a polyurethane catheter was performed on the right jugular vein of a Zucker fatty rat (8 weeks old, male, Charles River Laboratories Japan, Inc.), which is an obesity and insulin-resistant model, and experiments were performed in the following four groups.

(1) Control group: purified water was administered at a ratio of 5 ml/kg (2) Compound (I) group: the compound (I) dissolved in purified water was administered at a dose of 3 mg/kg (5 ml/kg)

(3) Miglitol group: Miglitol dissolved in purified water was administered at a dose of 3 mg/kg (5 ml/kg)

(4) Concomitant use group: the compound (I) and Miglitol dissolved in purified water were administered at respective dose of 3 mg/kg (5 ml/kg)

Figure 2:
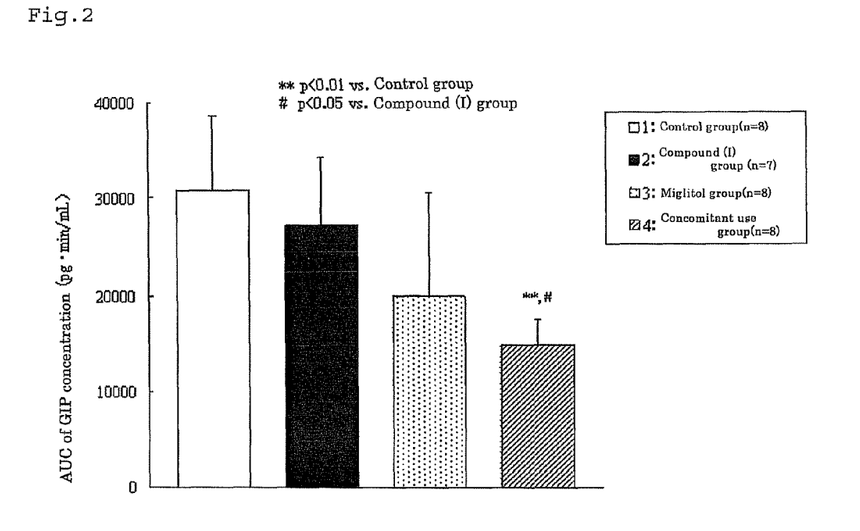
FIG. 2 is a graph showing the actions of the compound (I) alone, Miglitol alone and concomitant use of the compound (I) and Miglitol on the change of the plasma concentration of GIP after the liquid diet loading in Zucker fatty rats.
Figure 3:
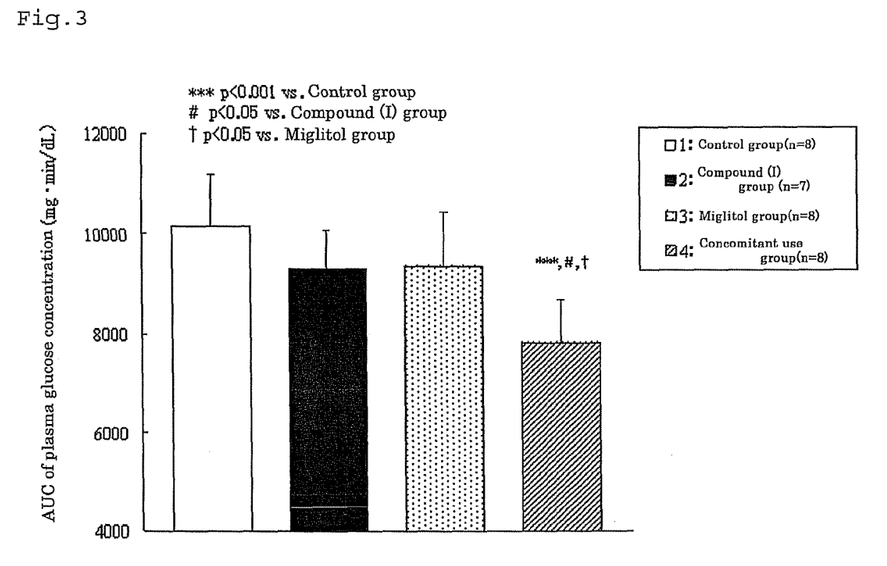
FIG. 3 is a graph showing the actions of the compound (I) alone, Miglitol alone and concomitant use of the compound (I) and Miglitol on the change of the blood glucose level after the liquid diet loading in Zucker fatty rats.
Figure 4:
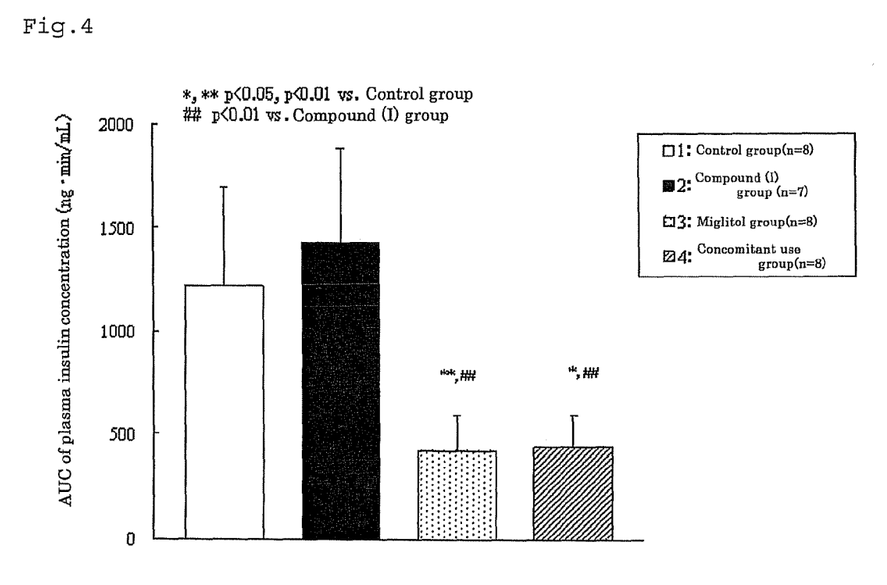
FIG. 4 is a graph showing the actions of the compound (I) alone, Miglitol alone and concomitant use of the compound (I) and Miglitol on the change of the plasma insulin concentration after the liquid diet loading in Zucker fatty rats.

Purified water, the compound (I) and Miglitol were orally administered respectively to the Zucker fatty rats fasted overnight in each group as described in (1) to (4), and after 15 minutes, a liquid diet (trade mark: ENSURE H, Meiji Dairies Corporation, Japan) was administered at a ratio of 10 ml/kg to carry out a diet loading test. Blood was collected from the catheter immediately before loading and after loading of the liquid diet, and centrifuged at 4° C., 3000 rpm for 10 minutes to obtain plasma. The GIP concentration in the obtained plasma was measured by an ELISA (RAT/MOUSE GIP (TOTAL) ELISA KIT, LINCO Research, Inc., US), and the plamsa glucose and insulin concentrations was measured by Glucose C2 (Wako Pure Chemical Industries, Ltd., Japan) and ELISA (Rat Insulin ELISA Kit, Shibayagi, Co., Ltd., Japan), respectively. Based on the measured GIP concentration in plasma, AUC from immediately before the loading of the liquid diet to 120 minutes after the loading was calculated. Based on the measured plasma glucose and insulin concentrations, AUC from immediately before the loading of the liquid diet to 60 minutes after the loading was calculated. In addition, GIP concentration in plasma shows the concentration of active GIP and inactive GIP in plasma. The result of the GIP concentration in plasma is shown in FIG. 2, the result of the plasma glucose level is shown in FIG. 3 and the result of the plasma insulin concentration is shown in FIG. 4. Each column in figure shows an average value (n=8 in Groups 1, 3 and 4, n=7 in Group 2)±a standard deviation.

(Result)
Plasma Glucose and Insulin Concentrations

For the effect of suppressing the plasma glucose concentration, there was no significant difference in single administration of the compound (I) or Miglitol. However, the compound (I) significantly suppressed increase in the plasma glucose concentration when concomitantly used with Miglitol. Furthermore, the insulin concentration in blood plasma was significantly decreased by concomitant use of the compound (I) and Miglitol. Namely, it is shown that the compound (I) significantly suppresses increase in the plasma glucose concentration without excess secretion of insulin when concomitantly used with Miglitol. Thus, effectiveness for hyperglycemia and impaired fasting plasma glucose by correction of glycemic control can be expected.

GIP Concentration in Blood Plasma

In the liquid diet loading test to Zucker fatty rats, there was no change in the increase in the GIP concentration in plasma by administering the compound (I), but Miglitol showed a tendency of suppressing. Furthermore, when the compound (I) and Miglitol were used concomitantly, the increase in the GIP concentration was significantly suppressed. Namely, it is shown that the compound (I) significantly suppresses the secretion of GIP when concomitantly used with Miglitol. Therefore, there may be expectations on effects in accordance with suppression of GIP secretion, for example, an action of lowering body weight, an action of improving insulin resistance, and the like.

Experimental Example 3

Effects of compound (I) alone, Metformin alone and concomitant use of compound (I) and Metformin on plasma concentrations of active GLP-1, glucose and insulin during oral corn starch loading test in ZDF-Lepr$^{fa}$/CrlCrlj rat (hereinafter abbreviated as ZDF rat)

(Test Method)

An operation to insert a polyurethane catheter was performed on the right jugular vein of a ZDF rat (13 weeks old, male, Charles River Laboratories Japan, Inc.), and experiments were performed in the following four groups.

(1) Control group: purified water was administered at a ratio of 5 ml/kg (2) Compound (I) group: the compound (I) dissolved in purified water was administered at a dose of 3 mg/kg (5 ml/kg)

(3) Metformin group: Metformin dissolved in purified water was administered at a dose of 300 mg/kg (5 ml/kg)

(4) Concomitant use group: the compound (I) and Metformin dissolved in purified water were administered at respective doses of 3 mg/kg (5 ml/kg) and 300 mg/kg (5 ml/kg)

Figure 5:
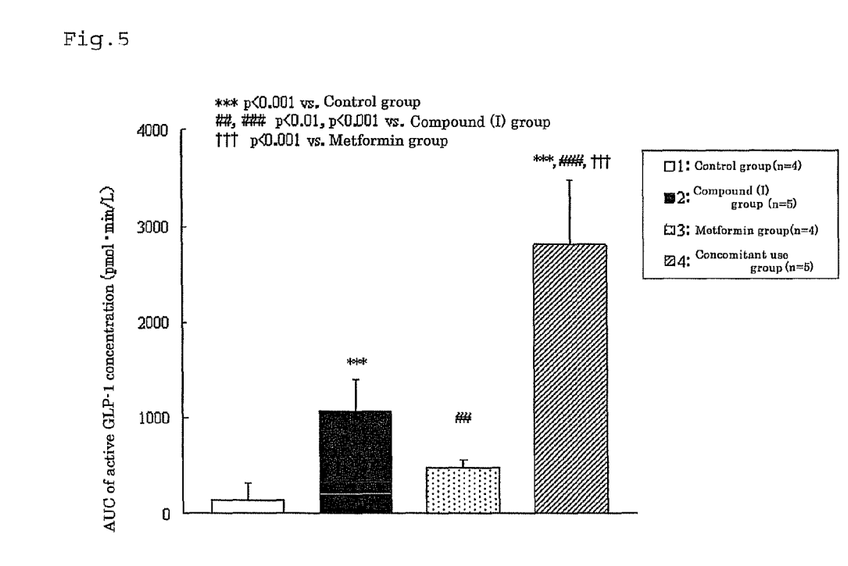
FIG. 5 is a graph showing the actions of the compound (I) alone, Metformin alone and concomitant use of the compound (I) and Metformin on the change in the increase in the plasma concentration of active GLP-1 after the oral corn starch loading in ZDF rats.
Figure 6:
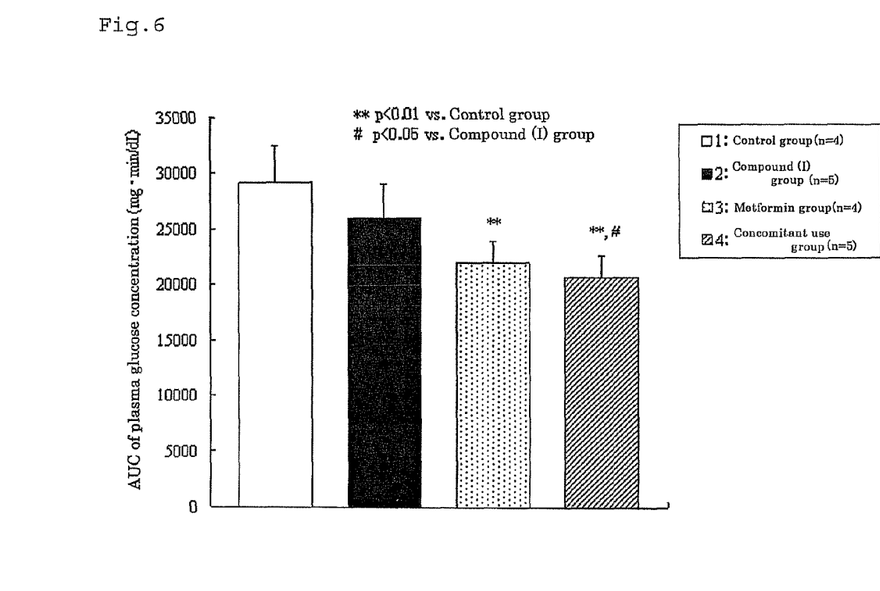
FIG. 6 is a graph showing the actions of the compound (I) alone, Metformin alone and concomitant use of the compound (I) and Metformin on the change of the blood glucose level after the oral corn starch loading in ZDF rats.
Figure 7:
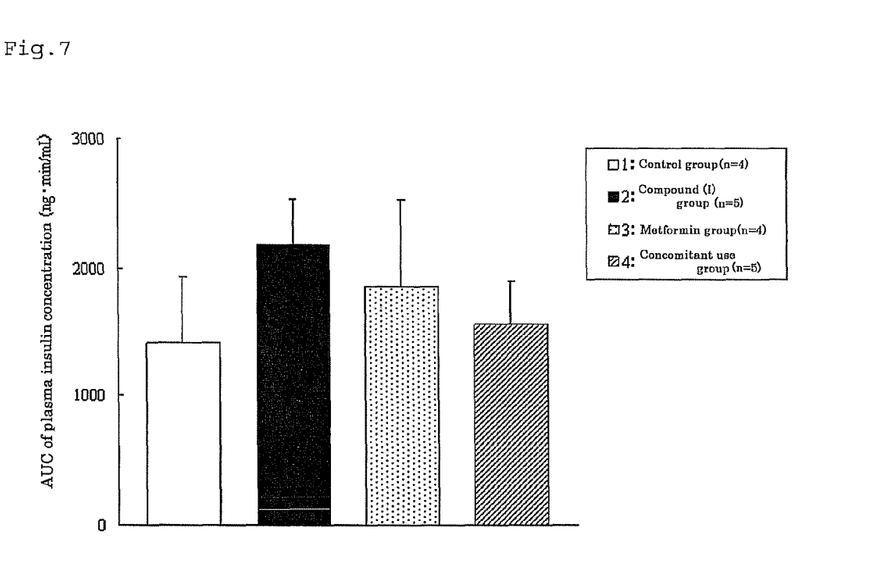
FIG. 7 is a graph showing the actions of the compound (I) alone, Metformin alone and concomitant use of the compound (I) and Metformin on the change of the plasma concentration of insulin after oral loading of corn starch in ZDF rats.

Purified water, the compound (I) and Metformin were orally administered respectively to the ZDF rats fasted overnight in each group as described in (1) to (4), and after 15 minutes, 0.4 g/ml corn starch suspension in purified water was administered at a ratio of 5 ml/kg. Blood was collected from the catheter immediately before administration and after administration of corn starch, and centrifuged at 4° C., 3000 rpm for 10 minutes to obtain plasma. The concentration of the active GLP-1 in the obtained blood plasma was measured by ELISA (GLUCAGON-LIKE PEPTIDE-1 (ACTIVE) ELISA KIT, LINCO Research, Inc., US), the plasma glucose and insulin concentrations of the obtained plasma was measured by Glucose C2 (Wako Pure Chemical Industries, Ltd., Japan) and ELISA (Rat Insulin ELISA Kit, Shibayagi, Co., Ltd., Japan), respectively. Based on the measured concentration of the active GLP-1 in the plasma, the amount of change relative to the concentration immediately before starch administration was obtained. Based on the amount of change relative to the plasma active GLP-1, glucose and insulin concentrations, AUC from immediately before the administration of starch to 180 minutes after the administration was calculated. The result of the plasma active GLP-1 concentration is shown in FIG. 5, the result of the plasma glucose concentration is shown in FIG. 6 and the result of the plasma insulin concentration is shown in FIG. 7. Each column in figure shows an average value (n=4 in Groups 1 and 3, n=5 in Group 2 and 4)±a standard deviation.

(Result)
Active GLP-1 Concentration

In the oral corn starch loading test to ZDF rats, there was no significant difference in the increase of the concentration of the active GLP-1 in the plasma by administration of Metformin, whereas the compound (I) increased the concentration significantly. Furthermore, when the compound (I) and Metformin were used concomitantly, the concentration of the active GLP-1 in the plasma was increased more than that when the compound (I) was used alone, and the degree thereof was synergistic. Namely, it is shown that an action of accelerating neogenesis or replication of pancreatic β cells or an action of lowering body weight can be expected by the concomitant use of the compound (I) and Metformin.

Plasma Glucose and Insulin Concentrations

For the effect of suppressing the plasma glucose elevation, there was no significant difference in administration of the compound (I) alone, but Metformin was significantly suppressed. Furthermore, when the compound (I) and Metformin were used concomitantly, the increase in the plasma glucose concentration was significantly suppressed more than that when the compound (I) was used alone. The insulin concentration in plasma at that time was significantly lowered. Namely, it is shown that the compound (I) significantly suppresses increase in the plasma glucose concentration without excess secretion of insulin when concomitantly used with Metformin. Thus, effectiveness for hyperglycemia and fasting plasma glucose disorder by correction of blood glucose control can be expected.

Experimental Example 4

Effects of compound (I) alone, Metformin alone and concomitant use of compound (I) and Metformin on concentration of GIP in plasma during oral corn starch loading test in Slc: Wistar/ST rats (hereinafter abbreviated as Wistar rats)
(Test Method)

An operation to insert a polyurethane catheter was performed on the right jugular vein of a Wistar rat (9 weeks old, male, Japan SLC, Inc.), and experiments were performed in the following four groups.

(1) Control group: purified water was administered at a ratio of 5 ml/kg (2) Compound (I) group: the compound (I) dissolved in purified water was administered at a dose of 3 mg/kg (5 ml/kg)

(3) Metformin group: Metformin dissolved in purified water was administered at a dose of 300 mg/kg (5 ml/kg)

(4) Concomitant use group: the compound (I) and Metformin dissolved in purified water were administered at respective doses of 3 mg/kg (5 ml/kg) and 300 mg/kg (5 ml/kg)

Figure 8:
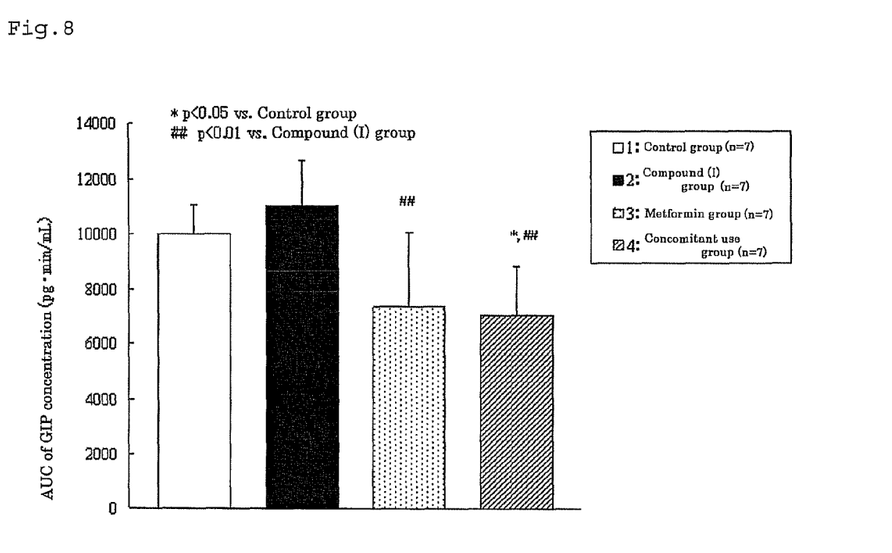
FIG. 8 is a graph showing the actions of the compound (I) alone, Metformin alone and concomitant use of the compound (I) and Metformin on the change of the plasma GIP concentration after the oral corn starch loading in Wistar rats.

Purified water, the compound (I) and Metformin were orally administered respectively to the Wistar rats fasted overnight in each group as described in (1) to (4), and after 30 minutes, 0.4 g/ml corn starch suspension in purified water was administered at a ratio of 5 ml/kg. Blood was collected from the catheter immediately before administration and after administration of corn starch, and centrifuged at 4° C., 3000 rpm for 10 minutes to obtain plasma. The concentration of the GIP in the obtained plasma was measured by ELISA (RAT/MOUSE GIP (TOTAL) ELISA KIT, LINCO Research, Inc., US). Based on the measured GIP concentration, AUC from immediately before the administration of starch to 180 minutes after the administration was calculated. The result of calculation was shown in FIG. 8. Each column in figure shows an average value (n=7)±a standard deviation.
(Result)
GIP Concentration in Plasma In the oral corn starch loading test to Wistar rats, there was no change in the increase in the concentration of GIP in plasma by the compound (I) administration, but Metformin was significantly suppressed. Furthermore, when the compound (I) and Metformin were used concomitantly, the increase in the concentration of GIP was significantly suppressed more than that when the compound (I) was used alone. Therefore, there may be expectations on effects in accordance with suppression of GIP secretion, for example, an action of lowering body weight, an action of improving insulin resistance, and the like.

INDUSTRIAL APPLICABILITY

The medicine of the present invention is useful as a therapeutic and/or prophylactic agent of type 2 diabetes, diabetic complications or impaired glucose tolerance, and the like, and is expected to be an excellent medicine for these diseases.

The invention claimed is:

1. A method for treating a disease selected from the group consisting of type 2 diabetes, impaired glucose tolerance, and insulin resistance, comprising administering to a patient an effective amount of (S)—N-(2-(2-(2-cyanopyrrolidin-1-yl)-2-oxoethylamino)-2-methylpropyl)-2-methylpyrazolo[1,5-a]pyrimidine-6-carboxamide, pharmaceutically acceptable salt thereof, or solvate thereof, and an effective amount of one or more other diabetic medicine selected from the group consisting of a biguanide and α-glucosidase inhibitor concomitantly.

2. The method according to claim 1, wherein the other diabetic medicine is a biguanide.

3. The method according to claim 2, wherein the biguanide is Metformin or a salt thereof.

4. The method according to claim 1, wherein the other diabetic medicine is an α-glucosidase inhibitor.

5. The method according to claim 4, wherein the α-glucosidase inhibitor is Miglitol.

6. A method for treating a disease selected from the group consisting of type 2 diabetes, impaired glucose tolerance, and insulin resistance, comprising administering to a patient an effective amount of (S)—N-(2-(2-(2-cyanopyrrolidin-1-yl)-2-oxoethylamino)-2-methylpropyl)-2-methylpyrazolo[1,5-a]pyrimidine-6-carboxamide, pharmaceutically acceptable salt thereof, or solvate thereof, in combination with an effective amount of one or more other diabetic medicine selected from the group consisting of a biguanide and α-glucosidase inhibitor.

7. The method according to claim 6, wherein the other diabetic medicine is a biguanide.

8. The method according to claim 7, wherein the biguanide is Metformin or a salt thereof.

9. The method according to claim 6, wherein the other diabetic medicine is an α-glucosidase inhibitor.

10. The method according to claim 9, wherein the α-glucosidase inhibitor is Miglitol.

* * * * *